US00PP16523P3

(12) United States Plant Patent
Trees

(10) Patent No.: US PP16,523 P3
(45) Date of Patent: May 9, 2006

(54) ***LANTANA* PLANT NAMED 'BALUCWHIT'**

(50) Latin Name: *Lantana camara*
Varietal Denomination: Balucwhit

(75) Inventor: Scott C. Trees, Shell Beach, CA (US)

(73) Assignee: Ball Horticultural Company, West Chicago, IL (US)

( * ) Notice: Subject to any disclaimer, the term of this patent is extended or adjusted under 35 U.S.C. 154(b) by 233 days.

(21) Appl. No.: 10/740,745

(22) Filed: Dec. 19, 2003

(65) Prior Publication Data

US 2005/0120447 P1 Jun. 2, 2005

Related U.S. Application Data

(60) Provisional application No. 60/503,333, filed on Sep. 16, 2003.

(51) Int. Cl.
*A01H 5/00* (2006.01)

(52) U.S. Cl. ..... Plt./227

(58) Field of Classification Search ..... Plt./227

See application file for complete search history.

*Primary Examiner*—Kent Bell
(74) *Attorney, Agent, or Firm*—Wood, Phillips, Katz, Clark & Mortimer

(57) ABSTRACT

A new and distinct *Lantana* plant named 'Balucwhit' characterized by its white-colored flowers, dark green-colored foliage, and upright and spreading growth habit.

1 Drawing Sheet

Latin name of genus and species of plant claimed: *Lantana camara.*
Variety denomination: 'Balucwhit'.

BACKGROUND OF THE INVENTION

The present invention relates to a new and distinct cultivar of *Lantana* plant botanically known as *Lantana camara* and hereinafter referred to by the cultivar name 'Balucwhit'.

The new cultivar was developed by the inventor in a controlled breeding program during April 2000, at Arroyo Grande, Calif. The objective of the breeding program was the development of *Lantana* cultivars with a well-branched and compact habit, continuous flowering and dark green-colored foliage.

The new cultivar was the product of the open pollination of the commercially available *Lantana* variety 'Simon Red' (not patented), characterized by its red/orange-colored flowers, and upright growth habit. 'Balucwhit' was selected in April 2001 at Arroyo Grande, Calif. as a single flowering plant within the progeny of the above stated open pollination and was initially designated '696-1'.

Asexual reproduction of the new cultivar by terminal stem cuttings taken since April 2001 at Arroyo Grande, Calif. and West Chicago, Ill. has demonstrated that the new cultivar reproduces true to type with all the characteristics, as herein described, firmly fixed and retained through successive generations of such asexual propagation.

SUMMARY OF THE INVENTION

The new cultivar has not been observed under all possible environmental conditions to date. Accordingly, it is possible that the phenotype may vary somewhat with variations in the environment, such as temperature, light intensity, and day length without, however, any variance in genotype.

It was repeatedly found that the cultivar of the present invention:

1. Exhibits white-colored flowers,
2. Forms dark green-colored foliage, and
3. Exhibits an upright and spreading growth habit.

Plants of the new cultivar differ from plants of the female parent primarily in flower color and growth habit.

Of the many commercially available *Lantana* cultivars known to the inventor, the most similar to 'Balucwhit' is 'Robpatdov' (U.S. Plant Pat. No. 10,882). However, in side-by-side comparisons, plants of 'Balucwhit' differ from plants of 'Robpatdov' in the following characteristics:

1. Plants of 'Balucwhit' have larger leaves than plants of 'Robpatdov'.
2. Plants of 'Balucwhit' have fewer inflorescences per plant than plants of 'Robpatdov', and
3. Plants of 'Balucwhit' have more flowers per inflorescence than plants of 'Robpatdov'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balucwhit'. The plants were grown for 10 weeks in a greenhouse at West Chicago, Ill.

DETAILED BOTANICAL DESCRIPTION

Figure 1:
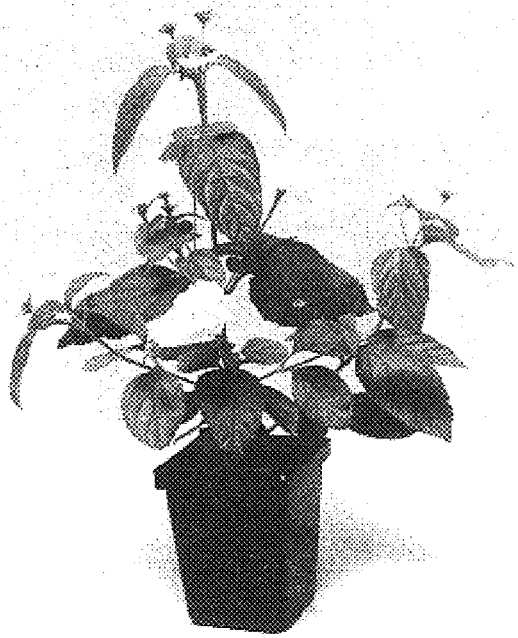
FIG. 1 illustrates a side view of the overall growth and flowering habit of 'Balucwhit'.
Figure 2:
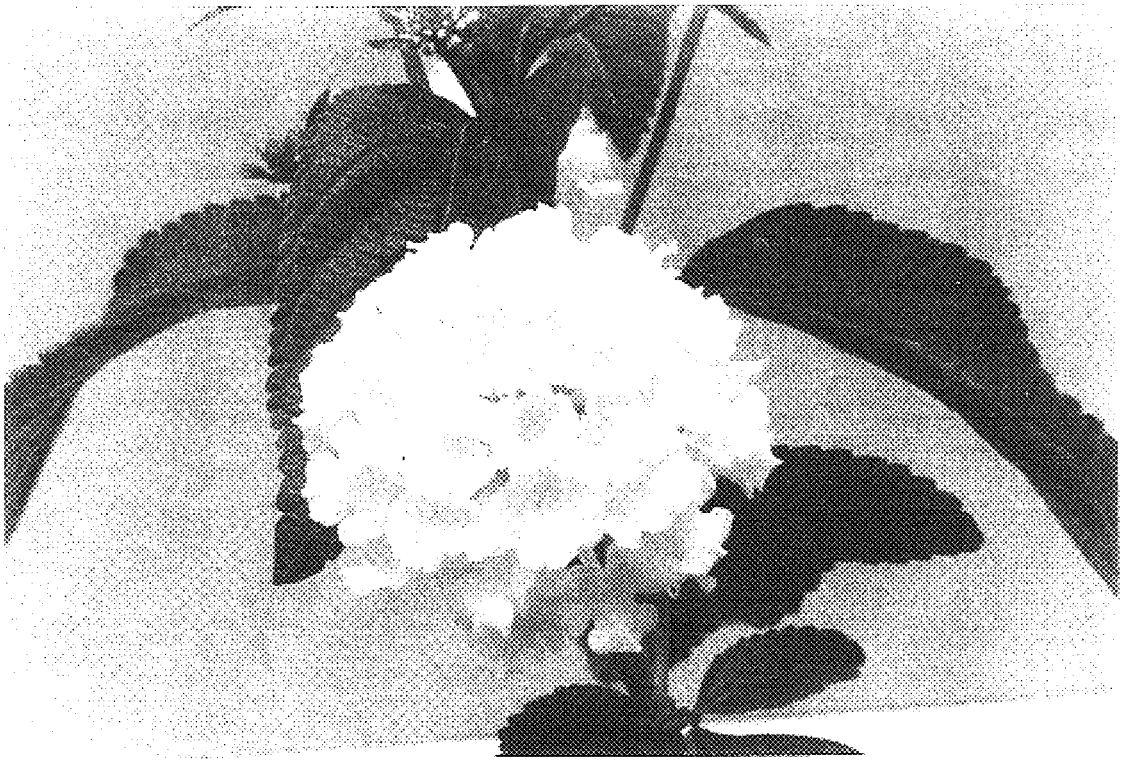
FIG. 2 illustrates a close-up view of a single inflorescence of 'Balucwhit'.

The chart used in the identification of colors described herein is The R.H.S. Colour Chart of The Royal Horticultural Society, London, England, 1995 edition, except where general color terms of ordinary significance are used. The color values were determined on Jul. 22, 2003. The readings were taken between 9:00 and 11:00 a.m. under natural day light conditions. The plants were produced from terminal stem cuttings taken from stock plants and were grown in a double polycarbonate-covered greenhouse in West Chicago, Ill. under conditions comparable to those used in commercial practice. The plants were grown in 10 cm pots for 10 weeks while utilizing a soilless growth medium. Greenhouse temperatures were maintained at approximately 75°–85° F. (24°–29° C.) during the day and approximately 62°–68° F. (17°–20° C.) during the night. Greenhouse light levels were maintained at 4,000 to 10,000 footcandles during the day.

Botanical classification: *Lantana camara* cultivar 'Balucwhit'.

Parentage: Open pollination of Simon 'Red' (not patented).

Propagation:

*Type cutting.*—Terminal stem cutting.

*Time to initiate roots.*—Approximately 7 to 11 days.

*Time to develop roots.*—Approximately 4 weeks.

*Root description.*—Fine, fibrous.

*Rooting habit.*—Freely branching.

Plant description:

*Habit of growth.*—Moderately vigorous. Forms lateral branches at every node. Pinching enhances basal branching. A mature plant, 10 weeks after the planting of a rooted cutting, measures approximately 31.9 cm in height from soil level to top of plant plane and approximately 35 cm in diameter (area of spread) with 3 main branches.

*Form.*—Upright and spreading.

*Branch.*—Shape: Quadrilateral. Strength: Strong. Length: Approximately 32.1 cm. Diameter: Approximately 3.3 mm. Texture: Hirsute. Color of young supple branch: 146C. Color of mature woody branch: N199A. Internode length at middle of stem is approximately 4.3 cm.

*Foliage.*—Type: Simple. Arrangement: Opposite. Orientation to stem: Obtuse. Fragrance: Faint, spicy. Shape: Ovate. Margin: Crenate. Apex: Acute. Base: Obtuse. Texture of upper surface: Moderately pubescent. Texture of lower surface: Densely covered with short, stiff hairs. Leaf length: Approximately 9.3 cm. Leaf width: Approximately 4.9 cm. Venation pattern: Pinnate. Color of upper surface of mature foliage: Closest to 147A with veins of 146D. Color of lower surface of mature foliage: 147B with veins of 146D. Petiole length: Approximately 1.2 cm. Petiole diameter: Approximately 2 mm. Petiole texture: Both surfaces: Moderately covered with short, stiff hairs. Petiole color: Both surfaces: Closest to 146D.

Flowering description:

*Flowering habit.*—Freely flowering.

*Natural flowering season.*—Year round in greenhouse environment and spring through autumn in outdoor garden.

Inflorescence description:

*Type.*—Corymb.

*Shape.*—Spherical.

*Size.*—Depth (height): Approximately 2.1 cm. Diameter: Approximately 3.8 cm. Number of flowers per inflorescence: Approximately 43 fully opened flowers at any one time.

*Bract.*—Each flower is subtended by a single bract. Shape: Linear. Length: Approximately 4 mm. Width: Approximately 0.6 mm. Apex: Acute. Margin: Entire. Texture: Lower surface is densely pubescent, upper surface is slightly pubescent with short hairs. Color of both surfaces is 144B.

*Peduncle.*—Shape: Quadrilateral. Length: Approximately 7.9 cm. Diameter: Approximately 1.5 mm. Angle to stem: Acute. Strength: Strong. Texture: Pubescent with very short glandular hairs and moderate amount of short stiff hairs. Color: 144A.

Flower description:

*Shape.*—Salverform. Buds open in progression from center to margin of inflorescence.

*Fragrance.*—Light, sweet.

*Aspect.*—Upward, outward.

*Lastingness of bloom.*—Approximately 5 days from first color on outer buds to last floret dropping.

*Bud.*—Shape: Roughly spherical. Length: Approximately 2.8 mm. Width: Approximately 2.8 mm. Color: 158A.

*Corolla size.*—Length: Approximately 1.2 cm. Width: Approximately 1 cm.

*Petals.*—Five, non imbricate, non-symmetrical, fused at base forming corolla tube. Shape: Obovate. Apex: Obtuse. Margin: Entire, ruffled. Color when first open: Upper surface: Lighter than 9D at margin, 9B around tube opening. Lower surface: 155D. Petal color when fully open: Upper surface: 155D at margin, 6D around tube opening. Lower surface: Lighter than 155D. Texture of upper and lower surfaces: Glabrous.

*Upper petal.*—Length from throat: Approximately 7 mm. Width: Approximately 8 mm.

*Lateral petal.*—Length from throat: approximately 7 mm. Width: Approximately 4 mm.

*Lower petal.*—Length from throat: Approximately 7 mm. Width: Approximately 7 mm. Corolla tube — Length: Approximately 1.3 cm. Diameter at tube opening: Approximately 1.5 mm. Diameter at base: Approximately 1 mm. Texture of outer surface: Densely covered with short hairs. Texture of inner surface: Glabrous except for hairs around opening. Color of outer surface: First open: 2C. Fully open: 5D. Color of inner surface: 155D.

*Calyx.*—Shape: Tubular, formed by 5 fused sepals with acute tips. Calyx length: Approximately 6 mm. Calyx diameter at apex: Approximately 1 mm. Sepal length: 6 mm. Sepal width: 1 mm. Sepal texture: Glabrous. Sepal color: 1D.

*Reproductive organs.*—Stamens: Four per flower, fused (adnate) to the corolla tube. Filament length of free portion: 2 mm. Filament color: 155D. Anther shape: 2 lobed. Anther length: 0.7 mm. Anther color: 162A. Amount of pollen: Moderate. Pollen color: 4D. Pistil quantity: One per flower. Pistil length: 3 mm. Stigma shape: Oval. Stigma length: 0.5 mm. Stigma color is 144C. Style length: Approximately 2 mm. Style color: 154D. Ovary length: 0.5 mm. Ovary color: 144C.

Seed and fruit production: Neither seed nor fruit production has been observed.

Disease and pest resistance: Resistance to pathogens or pests common to *Lantana* has not been observed.

Hardiness zone: 'Balucwhit' is hardy in zones nine (9) and above.

What is claimed is:

1. A new and distinct cultivar of *Lantana camara* plant named 'Balucwhit' substantially, as herein shown and described, which:

1. Exhibits white-colored flowers,
2. Forms dark green-colored foliage, and
3. Exhibits an upright and spreading growth habit.

* * * * *